United States Patent
Sidhu et al.

(10) Patent No.: US 8,231,384 B2
(45) Date of Patent: Jul. 31, 2012

(54) DENTAL EVACUATION TOOL

(75) Inventors: Jessy S. Sidhu, Las Vegas, NV (US); David Behoteguy, Brea, CA (US)

(73) Assignee: Jessy S. Sidhu, Professional Corporation, Las Vegas, NV (US)

( * ) Notice: Subject to any disclaimer, the term of this patent is extended or adjusted under 35 U.S.C. 154(b) by 128 days.

(21) Appl. No.: 12/614,345

(22) Filed: Nov. 6, 2009

(65) Prior Publication Data

US 2010/0203470 A1 Aug. 12, 2010

Related U.S. Application Data (63) Continuation-in-part of application No. 29/313,760, filed on Feb. 6, 2009, now abandoned.

(51) Int. Cl.
*A61C 17/06* (2006.01)

(52) U.S. Cl. .......................................................... 433/92

(58) Field of Classification Search ............... 433/91–96
See application file for complete search history.

(56) References Cited

U.S. PATENT DOCUMENTS

| | | | |
|---|---|---|---|
| 2,574,135 A | 11/1951 | Ward | |
| 2,637,106 A | 11/1951 | Otis | |
| 3,269,862 A | 10/1964 | Lanza et al. | |
| 3,460,255 A | 8/1969 | Hutson | |
| 3,650,827 A | 3/1972 | Brown et al. | |
| 3,890,712 A | 6/1975 | Lopez | |
| 4,041,207 A | 8/1977 | Takada et al. | |
| 4,155,823 A | 5/1979 | Gotcher et al. | |
| 4,265,621 A | 5/1981 | McVey | |
| D270,183 S | 8/1983 | Govenius | |
| 4,586,900 A * | 5/1986 | Hymanson et al. | 433/96 |
| 4,677,017 A | 6/1987 | De Antonis et al. | |
| 4,840,849 A | 6/1989 | Harada et al. | |
| 4,878,900 A * | 11/1989 | Sundt | 604/119 |
| D312,872 S | 12/1990 | Mahl | |
| 5,015,184 A * | 5/1991 | Perry et al. | 433/93 |
| 5,066,228 A | 11/1991 | Doundoulakis et al. | |
| 5,078,603 A | 1/1992 | Cohen | |
| 5,080,587 A | 1/1992 | Miyao | |
| 5,093,166 A | 3/1992 | Nishimura | |

(Continued)

FOREIGN PATENT DOCUMENTS

JP 10-262993 A 10/1998

OTHER PUBLICATIONS

Practicon Dental Full Line Catalog Fall 2001, cover page, p. 52, 2 pages total.

(Continued)

*Primary Examiner* — Heidi M Eide
(74) *Attorney, Agent, or Firm* — Knobbe, Martens, Olson & Bear LLP (57) ABSTRACT

Devices for connection to a dental evacuation system and methods of manufacturing the same. In one example, a dental evacuation device for connection to a dental evacuation system includes an elongated body having a central passageway extending through the body, a protective tip disposed over and extending from an end of the body member, and a screening device positioned within the central passageway. The protective tip can define an aperture configured to provide access to the central passageway and can include a blunt ridge circumscribing the defined aperture. In one example, the screening device is offset from the protective tip to form a receiving space within the central passageway therebetween.

31 Claims, 5 Drawing Sheets

U.S. PATENT DOCUMENTS

| | | |
|---|---|---|
| 5,094,616 A | 3/1992 | Levenson |
| 5,441,410 A | 8/1995 | Segerdal |
| 5,480,721 A | 1/1996 | Pozzoli et al. |
| 5,578,681 A | 11/1996 | Tabb |
| 5,688,121 A | 11/1997 | Davis |
| 5,741,134 A | 4/1998 | Davis |
| 5,916,659 A | 6/1999 | Koerber et al. |
| 6,068,477 A | 5/2000 | Mahlmann |
| 6,074,208 A * | 6/2000 | Mitchell .................. 433/91 |
| 6,129,547 A * | 10/2000 | Cise et al. ................ 433/80 |
| 6,183,254 B1 | 2/2001 | Cohen |
| 6,207,277 B1 | 3/2001 | Shieh |
| 6,241,521 B1 * | 6/2001 | Garrison ................. 433/140 |
| 6,280,415 B1 * | 8/2001 | Johnson .................. 433/91 |
| D478,383 S | 8/2003 | Timm et al. |
| 6,652,943 B2 | 11/2003 | Tukachinsky et al. |
| D496,724 S | 9/2004 | Myers et al. |
| 6,881,060 B2 | 4/2005 | Lundgren |
| D533,270 S | 12/2006 | Kierce et al. |
| D541,936 S | 5/2007 | Patterson |
| D546,451 S | 7/2007 | Givens, Jr. |
| D548,335 S | 8/2007 | Orsing |
| 7,335,023 B2 | 2/2008 | Mahlmann |
| 7,347,691 B1 | 3/2008 | Kelly, Sr. |
| 2003/0017433 A1 | 1/2003 | Reiz |
| 2006/0024641 A1 | 2/2006 | Mahlmann |
| 2006/0110702 A1 | 5/2006 | Mahlmann |
| 2008/0166684 A1 | 7/2008 | Kanas |

OTHER PUBLICATIONS

International Search Report dated Nov. 11, 2010; PCT/US2010/023393.

* cited by examiner

DENTAL EVACUATION TOOL

CROSS-REFERENCE TO RELATED APPLICATIONS

This application is a continuation-in-part of U.S. Design Patent Application Ser. No. 29/313,760, filed on Feb. 6, 2009, titled "DENTAL SUCTION TOOL," which is hereby expressly incorporated by reference in its entirety.

BACKGROUND

1. Field

Embodiments disclosed herein relate generally to dental tools. More specifically, certain embodiments concern devices that can be coupled with a source of negative pressure, for example, a suction system, to evacuate matter from a patient's mouth during a dental procedure.

2. Description of the Related Art

Dental professionals often use suction devices to evacuate or remove saliva, other fluids, biological debris, and other matter from the mouths of patients during various procedures. In procedures where a dental professional is required to evacuate a substantial amount of matter, a high volume evacuator (hereinafter, "HVE") device may be used. Embodiments disclosed herein relate to HVE devices and methods for evacuating matter from a patient's mouth during a dental procedure.

SUMMARY

The devices and methods disclosed herein each have several aspects, no single one of which is solely responsible for their desirable attributes. Without limiting the scope of the claims, some prominent features will now be discussed briefly. Numerous other embodiments are also contemplated, including embodiments that have fewer, additional, and/or different components, steps, features, objects, benefits, and advantages. The components, aspects, and steps may also be arranged and ordered differently. After considering this discussion, and particularly after reading the section entitled "Detailed Description of Certain Embodiments," one will understand how the features of the devices and methods disclosed herein provide advantages over other known devices and methods.

In one embodiment, a dental evacuation device for connection to a suction system may include, for example, an elongated body member, a protective tip, and a screening device. The elongated body member may include or be formed of, for example, a first material, the elongated body member extending along a longitudinal axis and having a connection end, a suction end, an inner surface, and an outer surface, wherein the inner surface defines a central passageway extending through the body member from the connection end to the suction end, a protective tip, and a screening device. The protective tip may include or be formed of, for example, a second material and the protective tip may be disposed over and extending from the suction end of the body member. The protective tip may define a suction aperture configured to provide access to the central passageway. The screening device can be positioned within the central passageway between the connection end and the suction end.

In certain aspects, the screening device can be offset from the suction end of the central passageway and comprise a receiving space disposed between the screening device and the suction end. The elongated body can also include a transverse aperture disposed between the suction end and the connection end, for example, between the screening device and the connection end. The elongated body can also include a securement aperture disposed between the suction and the connection end, for example, between the screening device and the suction end. At least a portion of the protective tip can be disposed within the securement aperture.

In other aspects, the screening device can be disposed on a plane that lies substantially normal to the longitudinal axis and the screening device can include a plurality of openings configured to allow the passage of liquids and gases through the screening device. The openings can be substantially polygonal, substantially curvilinear, and the like, for example. The openings can have a cross-sectional area, for example, of between about 0.5 and 4.0 square millimeters, for example, between about 2.0 and 2.5 square millimeters. The screening device can be separate from or integral with the elongated body member. At least a portion of the protective tip can be disposed over at least a portion of the inner surface and at least a portion of the protective tip can be disposed over a portion of the outer surface. In some aspects, the first material can be the same as the second material and in other aspects, the first material and the second material can be different. The first material can comprise or be formed of polypropylene and the second material can comprise or be formed of a thermoplastic elastomer, for example, ethylene propylene diene monomer rubber. The protective tip can include a blunted ridge circumscribing the suction aperture and the blunted ridge can comprise a distal contour, wherein the distal contour is not planar.

In another embodiment, a dental evacuation device for connection to a suction system can include, for example, an elongated member, a protective tip, and a screening device. The elongated member can include, for example, polypropylene and extend along a longitudinal axis. The elongated body can have a connection end, a suction end, an inner surface, and an outer surface, wherein the inner surface defines a central passageway extending through the member from the connection end to the suction end. The elongated body may have a transverse aperture disposed between the suction end and the connection end. The protective tip can include, for example, a cross-linked mixture of ethylene propylene diene monomer rubber and polypropylene. The protective tip can be disposed over and extending from the suction end of the elongated member, the protective tip defining a suction aperture configured to provide access to the central passageway. The protective tip can include, for example, a blunted ridge circumscribing the suction aperture. The screening device may be positioned within the central passageway between the transverse aperture and the connection end, the screening device comprising a plurality of openings configured to allow the passage of liquids and gases through the screening device, wherein the openings are substantially polygonal and have a cross-sectional area of between about 2.0 square millimeters and about 2.5 square millimeters, for example.

In yet another embodiment, a dental evacuation device for connection to a suction system may include, for example, an elongated body member, a protective means, and a screening means. The elongated body may have, for example, a connection end, a suction end, an inner surface, and an outer surface, wherein the inner surface defines a central passageway extending through the body member from the connection end to the suction end. The protective means can be disposed over a portion of the elongated body member for protecting a patient from the suction end of the elongated body member. The screening means can be positioned within the central passageway for screening matter passing therethrough.

In another embodiment, a dental evacuation system may include, for example, a delivery device configured to produce a source of negative pressure and a dental evacuation device. The dental evacuation device may include, for example, an elongated body member, a protective tip, and a screening device. The elongated body member may include, for example, a first material, extend along a longitudinal axis, and have a connection end, a suction end, an inner surface, and an outer surface, wherein the inner surface defines a central passageway extending through the body member from the connection end to the suction end. The protective tip may include, for example, a second material and be disposed over and extend from the suction end of the body member, the protective tip can define a suction aperture configured to provide access to the central passageway. The screening device can be positioned within the central passageway between the connection end and the suction end. The connection end can be configured to connect to the delivery device such that the dental evacuation device is exposed to the source of negative pressure.

Some embodiments relate to a method of evacuating material from a patient, for example, by providing an embodiment of an evacuation device disclosed herein and contacting the device with a patient to remove material from the patient.

In another embodiment, a method of manufacturing a dental evacuation device may include, for example, forming an elongated body member with a first material, the elongated body member having a first end, a second end, an inner surface, an outer surface, and a screen, wherein the inner surface defines a central passageway extending through the body member from the first end to the suction end; wherein the screen is positioned within the central passageway between the first end and the second end and forming a protective tip with a second material on the elongated body, the protective tip being attached to and extending from the second end of the body member and defining an aperture configured to provide access to the central passageway.

In certain aspects, the first material and the second material can be different. The first material can include, for example, polypropylene and the second material can include, for example, ethylene propylene diene monomer rubber. The elongated body member and/or protective tip can be injection molded, for example.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION OF CERTAIN EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Dental suction tools include high volume evacuator (HVE) devices and saliva ejector devices. HVE devices and saliva ejector devices can be coupled with a source of negative pressure, for example, a vacuum or suction system, in order to transfer matter from a first location to a second location. Generally, saliva ejector devices are configured to remove excess saliva from a patient's mouth during a dental procedural whereas HVE devices are configured to evacuate saliva and other matter from a patient's mouth during a dental procedure. For example, HVE devices can be used to evacuate saliva, other biological matter, and non-biological matter including, but not limited to, dental restorative materials and restorations. Accordingly, HVE devices are commonly formed from rigid materials, saliva ejector devices are formed from more flexible materials, and the central passageways in HVE devices are typically larger than the lumens or central passageways in saliva ejector devices.

Inserting an HVE device into a patient's mouth can lead to inadvertent traumas, for example, lacerations or hematomas, in the patient's mouth. In many cases, the dental professional and/or patient may not notice these traumas when they occur because the patient's mouth has been numbed by a local anesthesia. Traumas caused by HVE devices can result in post-procedure discomfort for the patient and/or other complications, for example, infections that are of the viral, bacterial, and fungal sort.

Additionally, certain materials, for example, biological and non-biological materials including materials that aid the dental professional during a procedure such as cotton rolls and gauze, can become lodged in the HVE device and/or suction system during a procedure and block the source of negative pressure or suction. To remedy such a blockage, the dental professional must stop working on the patient, turn the suction system off, disassemble or partially disassemble the HVE device and/or suction system, remove the blockage, reassemble the device, and turn the suction system on, before the professional can resume work on the dental procedure.

Moreover, in some situations, sterilized objects, for example, implants, grafts of the biologic sort (e.g., tissue and bone), and restorations, can inadvertently be evacuated through an HVE device and transported to an unsterile location, for example, a filter, within the suction system. In these circumstances, the dental professional must spend a great deal of time re-sterilizing the evacuated object before it can be put into the patient's mouth. Because many dental professionals see patients in ten or fifteen minute increments, delays due to HVE device/system blockages and/or dental restoration (e.g., crowns, veneers, inlays, onlays, and implants) retrievals can be costly to the dental professional and burdensome for the dental professional's patients. Furthermore, in some cases, large objects that are inadvertently evacuated with an HVE device can damage the suction system. Such damage can result in longer delays while the equipment is repaired in addition to substantial repair costs.

Embodiments disclosed herein generally relate to HVE devices configured to evacuate saliva and other matter, for example, from a patient's mouth during a dental procedure. Some embodiments disclosed herein relate to HVE devices that comprise protective tips disposed on the device and configured to inhibit inadvertent traumas caused by the HVE device during a dental procedure. Additionally, various embodiments disclosed herein relate to HVE devices that comprise screening devices configured to prevent blockages in HVE devices and/or suction systems. Certain embodiments disclosed relate to HVE devices that comprise a receiving space disposed between a screening device and a suction tip to catch larger objects that are inadvertently evacuated with an HVE device and prevent the larger objects from further evacuation through the un-sterile suction system.

Several non-limiting examples of embodiments will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments. Furthermore, embodiments can include several novel features, no single one of which is solely responsible for its desirable attributes or which is essential to practicing the technology herein described.

Figure 1:
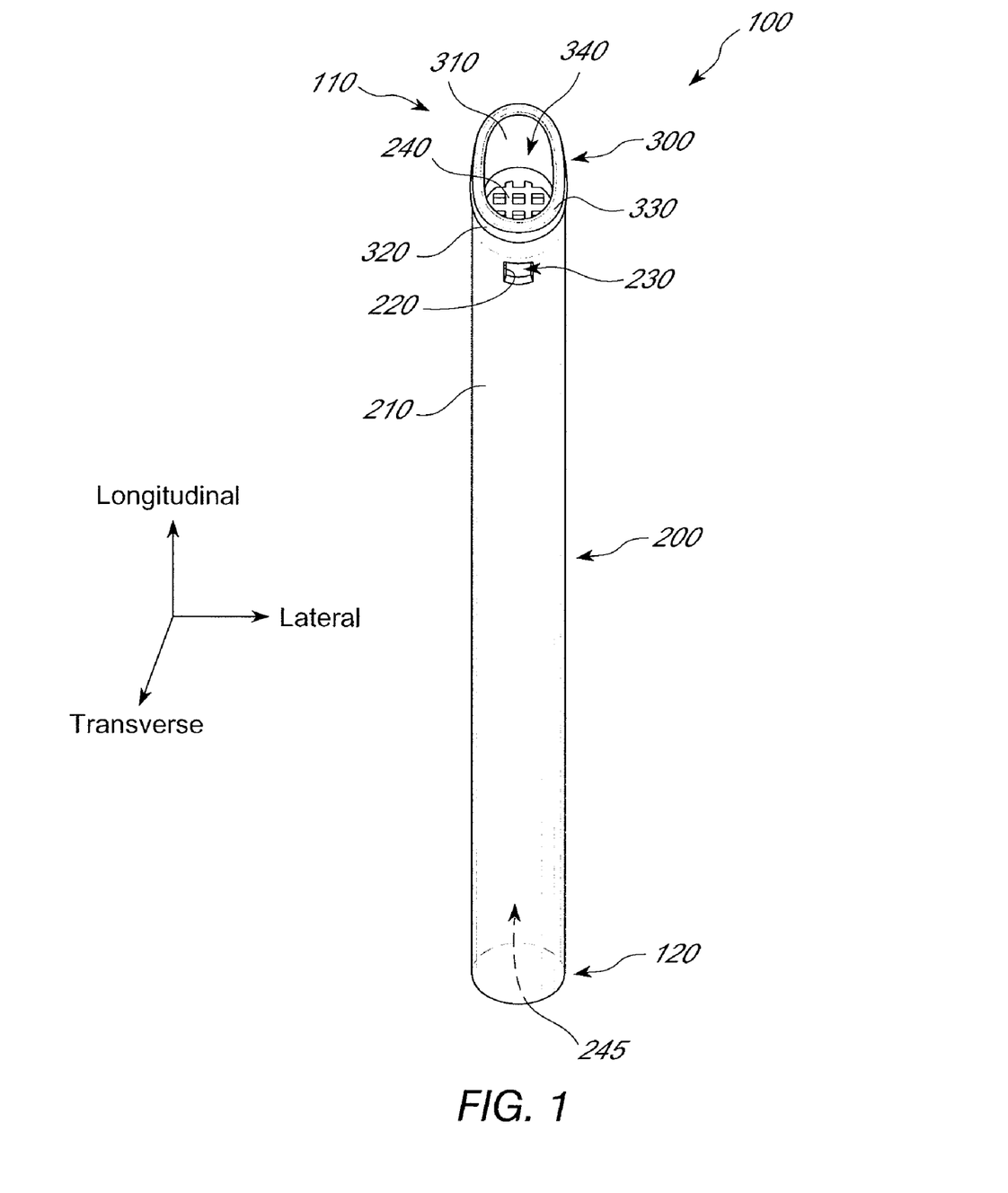
FIG. 1 is a front perspective view of one example of an embodiment of a dental suction tool including a protective tip and a screening device.

FIG. 1 schematically illustrates one example of an embodiment of a dental evacuation device 100. The device 100 has a suction end 110 and a connection end 120 disposed opposite to the suction end. The connection end 120 may be configured to releasably attach to a source of negative pressure, for example, a suction or vacuum system. The suction end 110 can receive matter from a patient's mouth and the received matter can be evacuated through the device 100 during a dental procedure when the connection end 120 is attached to a source of negative pressure. The device 100 can include a length dimension defined, for example, between the most distal point of the suction end 110 and the most proximal point of the connection end 120. The length dimension can vary. For example, non-limiting ranges for the length dimension may be between about 3 and about 30 centimeters and between about 13 and 16 centimeters. In one embodiment, the length dimension of the device is about 14.5 centimeters. The recited lengths are not limiting and one of skill in the art will appreciate, in view of the disclosure, that the length can longer or shorter than the recited numbers in some embodiments.

The dental evacuation device 100 includes an elongated body 200. The elongated body 200 can be generally tube shaped and include an outer surface 210 and an inner surface 220. The inner surface defines a central passageway or lumen 245 extending through the body 200 from the suction end 110 to the connection end 120 in a direction substantially parallel to the longitudinal axis of the device 100. The cross-section of the central passageway 245 can be generally polygonal, for example, rectangular, generally curvilinear, for example, round, oval, or circular, or generally polygonal and curvilinear. Similarly, the cross-section of the elongated body 200 can be generally polygonal, for example, rectangular, generally curvilinear, for example, round, oval or circular, or generally polygonal and curvilinear. The central passageway 245 can have a uniform cross-section along the longitudinal axis of the elongated body 200 or the central passageway 245 can have a non-uniform cross-section along the longitudinal axis of the elongated body 200. For example, the central passageway 245 can taper or narrow from one of the elongated body 200 towards the other end. In other embodiments, the cross-section of the central passageway 245 is substantially the same along the longitudinal axis of the elongated body 200.

In embodiments where the cross-section of the central passageway 245 is uniform along the length of the longitudinal axis, the area of the cross-section of the central passageway 245 can vary from embodiment to embodiment. For example, non-limiting ranges for the area of the cross-section of the central passageway 245 are between about 25 and about 3000 square millimeters. In one embodiment, the cross-section of the central passageway 245 may have an area of about 64 square millimeters. The width of the central passageway 245 can also vary. For example, non-limiting ranges for the width of the central passageway 245 are between about 5 and about 30 millimeters and between about 8 and about 10 millimeters. In one embodiment, the width of the central passageway 245 is about 9 millimeters. The recited numbers are not to be limiting. One of skill in the art will appreciate, in view of the disclosure, that the values can be greater or lesser than the recited numbers in some embodiments.

The elongated body 200 can be configured to be generally rigid and can be formed of generally rigid materials including, but not limited to, polymers, plastics, thermoplastics, composite materials (e.g., carbon fiber reinforced plastic), organic materials, cellulosic materials, rubbers, metals, and the like. For example, in some embodiments, the elongated body comprises a United States Food and Drug Administration approved polypropylene that is not affected by bodily fluids and can be easily sterilized.

The elongated body 200 can optionally include a transverse aperture or vent 230. The vent 230 can be disposed in a side of the elongated body 200 in order to connect the central passageway 245 with the outside of the dental evacuation device 100. The vent 230 can be configured to provide vacuum or suction relief to the central passageway 245, for example, in order to alleviate a high negative pressure which makes it difficult to remove the suction end 110 if it attaches to any tissue inside the patient's mouth or to their lips. In some embodiments, the elongated body 200 includes a plurality of vents 230 disposed circumferentially around the elongated body 200. The vent 230 or plurality of vents can be any shape, including, for example, generally square, rectangular, oval, round, and the like.

In the illustrated embodiment, the elongated body 200 includes a screening device 240 disposed within the central passageway 240. The screening device 245 can be integral with the elongated body 200 or can be a separate component, for example. As discussed in further detail below, the screening device 240 can be configured to block and/or catch objects that are over a certain size and prevent such objects from passing through the central passageway 245.

Still referring to FIG. 1, the dental evacuation device 100 includes a protective tip 300 disposed over the elongated body 200 at the suction end 110 of the device 100. The protective tip 300 can be disposed over at least a portion of the outer surface 210. The protective tip 300 can be disposed over at least a portion of the inner surface 220. The portion of the protective tip 300 that is disposed over the outer surface 210 of the elongated body 200 can be referred to as the external portion 320 of the tip. Similarly, the portion of the protective tip 300 that is disposed over the inner surface 220 of the elongated body 200 can be referred to as the internal portion 310 of the tip. Although the protective material is shown covering only a portion of the device, it should be understood that the protective material can cover any amount of the device up to, for example 100%. In some aspects the entire body, for example, can be made of or coated with a suitable protective material, including the materials described herein. For example, from 5% to about 100% of the exterior of the elongated body may be made of, coated or covered by a protective material.

The protective tip 300 can include at least one distal contour or face 330 disposed between the internal portion 310 and external portion 320. The distal contour 330 can be generally blunt to minimize the sharpness of the protective tip 300. The shape of the protective tip 300 can vary. For example, in some embodiments, the protective tip 300 can be formed such that the distal contour 330 is substantially planar. In other embodiments, the protective tip 300 can be formed such that the distal contour 330 is not substantially planar, for example. In some embodiments, the shape of the protective tip 300 can depend, in part, on the shape of the distal end of the elongated body 200. The interface between the distal contour 330 and internal portion 310 can define a suction aperture 340 configured to receive matter therethrough. The suction aperture 340 can provide access to the central passageway 245 such that matter can pass through the protective tip 300 into the central passageway 245.

Figure 2:
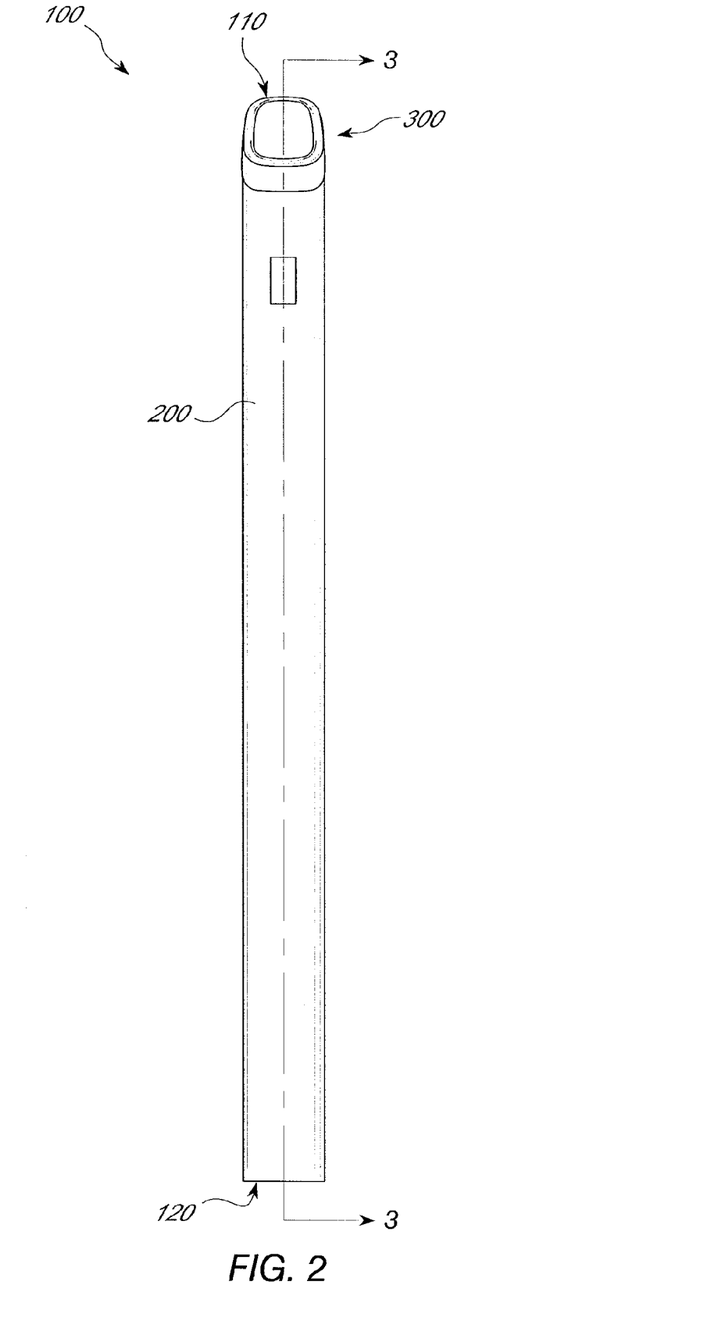
FIG. 2 is a front view of the dental suction tool of FIG. 1.

Turning now to FIG. 2, a front view of the example embodiment of FIG. 1 is shown. In use, the device 100 can be coupled with a suction system at the suction end 120 and the suction end 110 and protective tip 300 can be inserted into a patient's mouth to evacuate matter therefrom. After the dental procedure is over, the device 100 can be decoupled from the suction system and discarded or sterilized for subsequent use. The protective tip 300 can be formed of any suitable material to provide protection to the mouth of the patient. For example, the protective tip 300 can be formed of a relatively soft material configured to protect a patient from the sharper and more rigid elongated body 200. A non-limiting list of suitable materials for the protective tip 300 includes thermoplastic elastomers, rubbers, vulcanizates, and the like. In some embodiments, the protective tip 300 can include, for example, a cross-linked mixture of ethylene propylene diene monomer (EPDM) rubber and polypropylene, for example, SANTOPRENE™. The selection of the material of the protective tip 300 and the blunt shape of the tip can act in concert to protect a patient's mouth from trauma induced by the device 100.

Figure 3A:
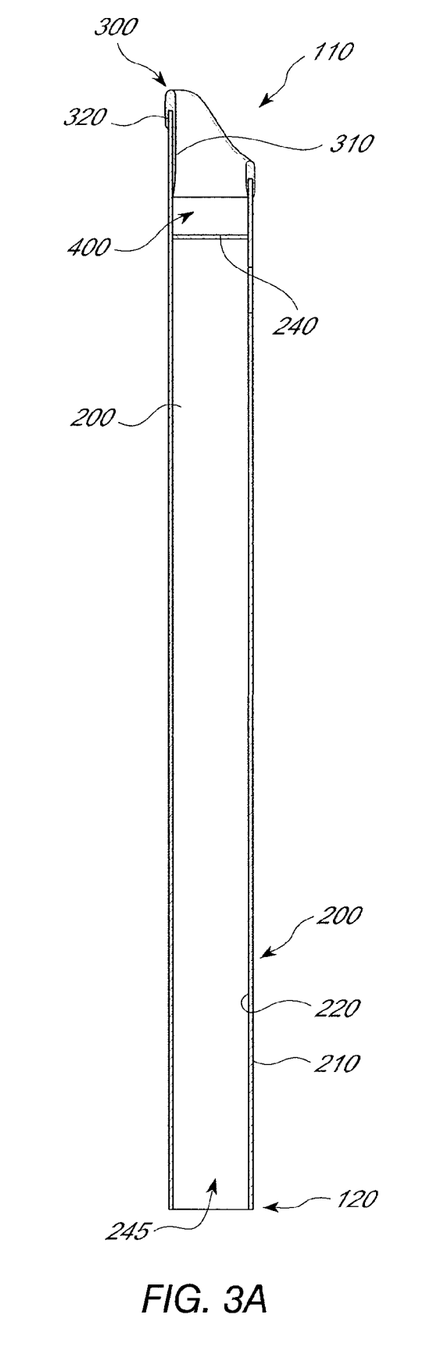
FIG. 3A is a cross-section of the dental suction tool of FIG. 1 taken along the line 3-3.

Turning now to FIG. 3A, a cross-section of the example embodiment of FIG. 1 is shown taken along the line 3-3 of FIG. 2. As discussed above, the screening device 240 can be disposed within the passageway 245 between the suction end 110 and the connection end 120 of the device 100. In some aspects, without being limited thereto, the screening device 240 can be offset from the most distal point of the suction end 110 by about 0.50 centimeters to about 6 centimeters or any distance therebetween, for example. In some embodiments, the screening device 240 can be offset from the most distal point on the suction end 110 by about 1.0 to about 3.0 centimeters. In some embodiments, the screening device 240 can be offset from the most distal point on the suction end 110 in terms of a percentage of the entire length of the device 100. For example, the screening device 240 can be offset from the most distal point on the suction end 110 by a distance that is between about 5% and about 95% of the entire length of the device 100. In some embodiments, the screening device 240 can be offset from the most distal point on the suction end 110 by a distance that is between about 5% and about 25% of the entire length of the device, for example, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% of the entire length. In some embodiments, the screening device 240 can be offset from the suction end 110 to create a receiving space 400 within the central passageway 245. For example, the receiving space 400 can be the entire volume of space from the screening device 240 to the suction end.

Figure 3B:
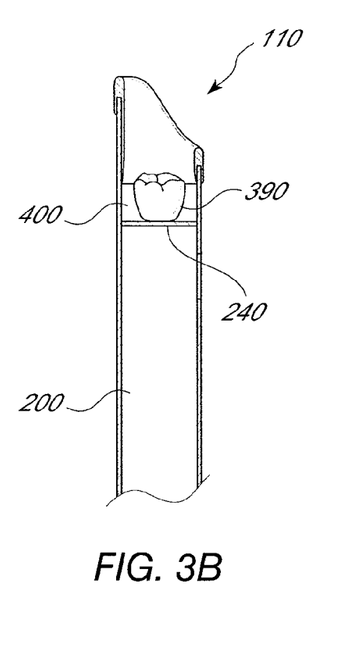
FIG. 3B is a cross-section of the dental suction tool of FIG. 1 taken along the line 3-3 with a crown received within the tool.

As schematically depicted in FIG. 3B, the receiving space 400 can be configured to receive and house objects, for example, a crown 390, that are evacuated through the suction end 110 of the device but cannot pass through the screening device 240. For example, in some embodiments the screening device 240 can be configured to prevent biologic and non-biologic materials including, but not limited to, cotton balls, pieces of gauze, dental restorations, for example, dental implants, dental implant components, and the like from passing therethrough. Dental implants, components of a dental implant, or dental restorations that are evacuated from a patient's mouth by the device 100 can be received and stored within the receiving space 400 until a dental professional removes the received component, implant, or restoration from the device 100. Accordingly, in FIG. 3, a dental professional can remove the received crown 390 from the receiving space 400 instead of having it pass through the device 100 and into the attached suction system. Thus, the receiving space 400 can act as a catch mechanism and prevent blockages of the device 100 or attached suction system, damage to the suction system, and/or loss of sterilized dental objects.

Still referring to FIG. 3, the internal surface 310 of the protective tip 300 can be larger than the external surface 320 such that the protective tip extends further down the inner surface 220 of the elongated body 200 than the outer surface 210. The internal surface 310 can act to protect objects that are received within the receiving space 400 from the more rigid and hard elongated body 200. In other embodiments, the internal surface 310 and external surface 320 of the protective tip 300 can be equally sized.

Figure 4:
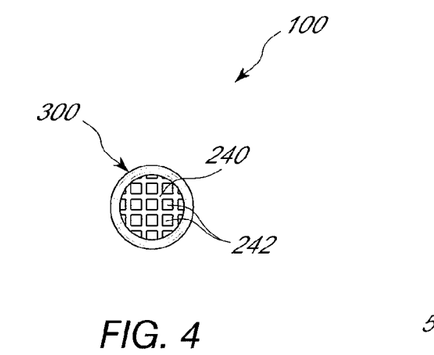
FIG. 4 is a top plan view of the dental suction tool of FIG. 1.

Turning now to FIG. 4, a top view of the dental evacuation device 100 of FIG. 1 is schematically depicted showing the screening device 240 disposed within the device 100. The screening device 100 can act as a screen, filter, sieve, sifter, or sorter to prevent objects over a certain size from passing through the device 100 to the attached suction system. As mentioned above, screening larger objects can prevent blockages within the device 100 or suction system and can also prevent damage to the suction system caused by the evacuation of larger solid objects. Also, the screening device 240 and elongated body can act to catch dental objects and restorations, for example, custom dental implants or sterilized components, before the objects are evacuated through the device 100 into the suction system.

The screening device 240 can include openings 242 configured to allow fluids biologic and non-biologic, air, other gases, and objects smaller than a certain size to pass through the screening device. The size and shape of the openings 242 can vary. In some embodiments, the openings 242 may be similarly sized and shaped. For example, the screening device can include a fine screen or mesh. The openings can be of any suitable size, for example, to block or capture desired materials, while permitting sufficient suction and passage of materials such as saliva and blood, for example. For example, the openings 242 can be substantially polygonal and have an area between about 0.5 and about 4.0 square millimeters. In some embodiments, the openings 242 are generally rectangular and have an area between about 2.0 and 2.5 square millimeters, for example, an area of about 2.0, 2.05, 2.1, 2.15, 2.2, 2.25, 2.3, 2.35, 2.4, 2.45, or 2.5 square millimeters. In one embodiment, the openings are generally rectangular have an area of about 2.25 square millimeters, for example. In another embodiment, the openings are generally round with an area of between about 2.0 and 2.5 square millimeters, for example. In other embodiments, a screening device 240 can include openings 242 that are differently shaped. For example, a first opening 242 can be generally curvilinear and a second opening 242 can be generally polygonal.

In some aspects the screening device 240 can include parallel openings or a "grate" type configuration, rather than the cross hatched design that is depicted, for example. Any suitable design can be used that can block or capture objects that are sucked into the device, but which should not pass into the suction apparatus. The size and shape of the openings 242 can be selected based in part on the dental procedure and the technical specifications of the suction system. For example, if the suction system the device 100 connects to is not capable of evacuating objects having a cross-sectional area over a certain size, the openings 242 can be configured to be smaller than the certain size to inhibit damage to and/or prevent malfunction of the suction system. The size and shape of the openings 242 can also be selected to maximize the efficiency of suction through the screening device 240. For example, the size and shape of the openings 242 can be configured to maximize the negative pressure or suction through the screening device 240 while simultaneously acting to filter, screen, or catch objects.

Figure 5:
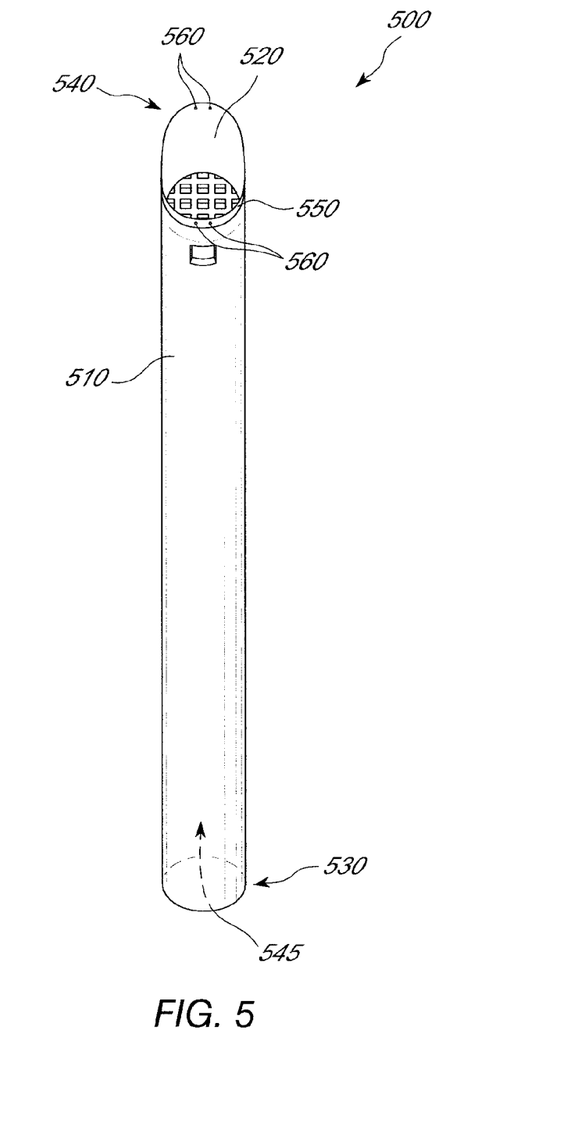
FIG. 5 is a perspective view of one example of an embodiment of an elongated body used to manufacture a dental suction tool.

Turning now to FIG. 5, one example of an embodiment of an elongated body 500 used to form a dental evacuation device is schematically illustrated. The elongated body 500 is generally tubular and includes an outer surface 510 and an inner surface 520. The inner surface 520 defines a central passageway 545 running through the body 500 between a distal end 540 and a proximal end 530. The elongated body 500 can be formed using a variety of suitable methods, including for example, injection molding. In some embodiments, the elongated body 500 may include, for example, a rigid polypropylene.

The elongated body 500 can also include a depressed or inset region 550 disposed near the distal end 540 in the outer surface 510. The depressed region 550 can be used to define a space or area for molding, or otherwise attaching, a protective tip (not shown) to the elongated body 500. The elongated body can also include one or more securement or engagement apertures 560 disposed near the distal end 540 and extending through the outer surface 510 and inner surface 520. The securement apertures 560 can be configured to receive a portion of a protective tip (not shown) to secure the protective tip relative to the elongated body 500. In some embodiments, a protective tip can be over-molded to the elongated body 500 and the liquid material that forms the tip can seep through the securement apertures 560 during the injection molding process such that the formed protective tip extends through the apertures 560 in the elongated body 500. In some embodiments, the elongated body 500 can be released from a mold using a release agent, for example, a silicone release agent. One having skill in the art will understand that the devices and components disclosed herein can be formed using a variety of suitable methods. Thus, the elongated body 500 does not have to include a depressed region 550 or securement apertures 560. Similarly, some embodiments of HVE devices disclosed herein can be manufactured as a single piece.

Some embodiments relate to methods of using the devices described herein. Some embodiments relate to methods of performing dental procedures or medical procedures using a device as described herein. For example, some embodiments relate to methods of evacuating material from the mouth of a patient by providing a device as described herein with instructions for attaching the device to a suction apparatus and/or instructions for using device during a dental procedure. The methods can include methods and instructions for removal of debris from the receiving space of a device, etc. The methods can include inserting and/or instructions for contacting the device with or inserting the device into the body of the patient, for example, the mouth, and removing material such as saliva, blood and other matter from the patient. The methods can include connecting and/or instructions for connecting the device with a suction system, vacuum system, negative pressure system, and/or pressure delivery system. In some embodiments, the device can be frictionally connected with a delivery system by sliding the device over a portion of the delivery system and/or by sliding a portion of the device within the delivery system. The methods can also include disconnecting and/or instructions for disconnecting the device with a suction system, vacuum system, negative pressure system, and/or pressure delivery system.

Some embodiments relate to kits that include, for example, a device as described herein and optionally instructions for using the device. The kits further optionally may include adaptors for fitting or attaching the devices onto a suction apparatus. Some embodiments relate to a suction apparatus that includes one or more devices as described herein. The kits can also include a plurality of devices as described herein packaged together. The plurality of devices can be packaged together in boxes, bags, plastic sheets, and/or other housings. For example, a kit can include between 2 and 10,000 of the devices described herein. In some embodiments, a kit can include 5, 10, 25, 50, 100, 150, 200, 250, 500, 1,000, 1,500, 2,000, 2,500, 5,000, or 10,000 of the devices disclosed herein.

Figure 6:
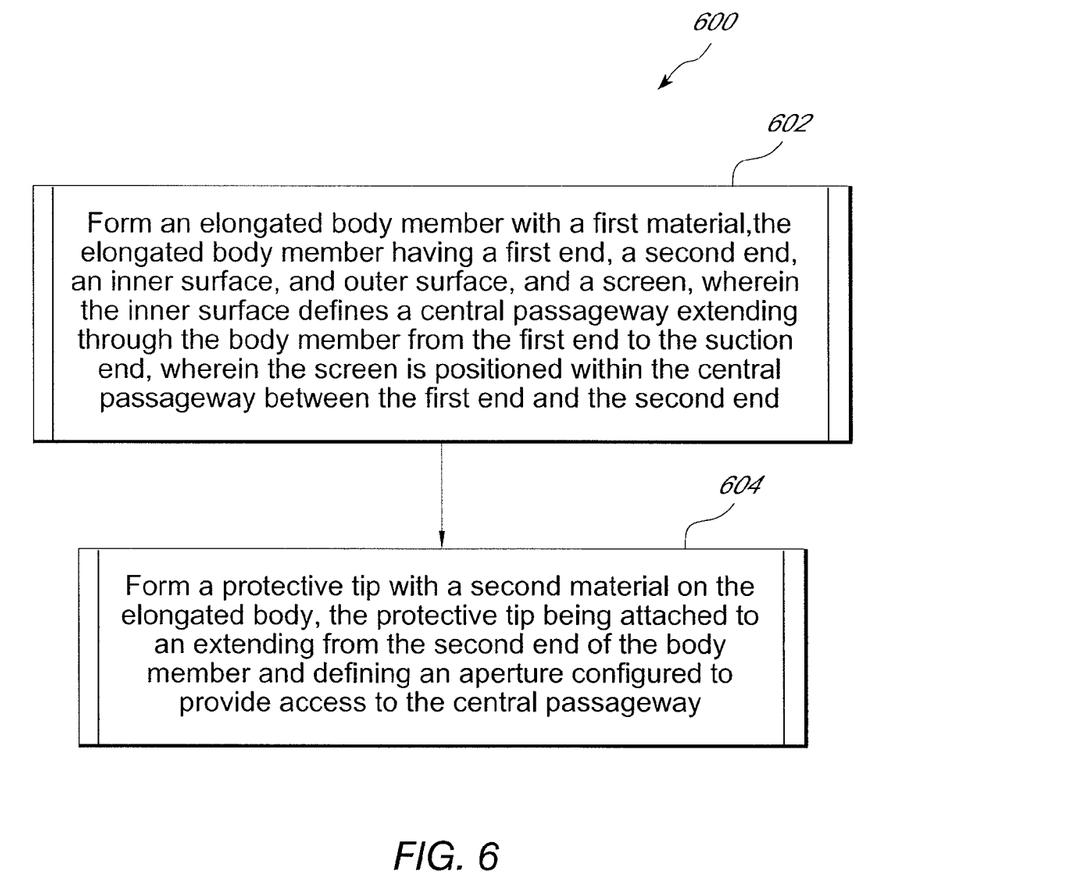
FIG. 6 is a flow diagram illustrating certain steps in an embodiment of a method of manufacturing a dental suction tool.

FIG. 6 is a block diagram schematically depicting a method 600 of manufacturing a dental evacuation device, according to one embodiment. Method 600 includes the steps of forming an elongated body member with a first material, the elongated body member having a first end, a second end, an inner surface, an outer surface, and a screen, wherein the inner surface defines a central passageway extending through the body member from the first end to the suction end, wherein the screen is positioned within the central passageway between the first end and the second end as illustrated in block 602 and forming a protective tip with a second material on the elongated body, the protective tip being attached to and extending from the second end of the body member and defining an aperture configured to provide access to the central passageway as illustrated in block 604. Those of skill in the art will understand and appreciate that the various embodiments of dental evacuation devices disclosed herein can be manufactured using a variety of different methods.

The foregoing description details certain embodiments of the devices and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A dental evacuation device for connection to a suction system, the evacuation device comprising:
   an elongated body member comprising a first material, the elongated body member extending along a longitudinal axis and having a connection end, a suction end, an inner surface, and an outer surface including a depressed region, the depressed region being depressed toward the longitudinal axis relative to another portion of the outer surface, wherein the inner surface defines a central passageway extending through the body member from the connection end to the suction end;
   a protective tip comprising a second material, the protective tip being non-releasably secured relative to the body member and disposed at least partially within the central passageway and over the depressed region of the body member, the protective tip extending from the suction end of the body member, the protective tip defining a suction aperture configured to provide access to the central passageway; and
   a screening device positioned within the central passageway between the connection end and the suction end.

2. The evacuation device of claim 1, wherein the screening device is offset from the suction end and the central passageway comprises a receiving space disposed between the screening device and the suction end.

3. The evacuation device of claim 1, wherein the elongated body further comprises a transverse aperture disposed between the suction end and the connection end.

4. The evacuation device of claim 1, wherein the body member comprises a transverse aperture disposed between the screening device and the connection end.

5. The evacuation device of claim 4, wherein the elongated body comprises a securement aperture disposed between the suction end and the connection end and extending transversely through the elongated body.

6. The evacuation device of claim 5, wherein the securement aperture is disposed between the screening device and the suction end.

7. The evacuation device of claim 6, wherein at least a portion of the protective tip is disposed within the securement aperture.

8. The evacuation device of claim 1, wherein the screening device is disposed on a plane that lies substantially normal to the longitudinal axis.

9. The evacuation device of claim 1, wherein the screening device comprises a plurality of openings configured to allow the passage of liquids and gases through the screening device.

10. The evacuation device of claim 9, wherein the openings are substantially polygonal.

11. The evacuation device of claim 9, wherein the openings are substantially curvilinear.

12. The evacuation device of claim 9, wherein the openings have a cross-sectional area of between about 0.5 and about 4.0 square millimeters.

13. The evacuation device of claim 1, wherein the screening device is integral with the elongated body member.

14. The evacuation device of claim 1, wherein the first material is the same as the second material.

15. The evacuation device of claim 1, wherein the first material and the second material are different.

16. The evacuation device of claim 15, wherein the first material comprises polypropylene.

17. The evacuation device of claim 16, wherein the second material comprises a thermoplastic elastomer.

18. The evacuation device of claim 17, wherein the thermoplastic elastomer comprises ethylene propylene monomer rubber.

19. The evacuation device of claim 1, wherein the protective tip comprises a blunted ridge circumscribing the suction aperture.

20. The evacuation device of claim 19, wherein the blunted ridge comprises a distal contour, wherein the distal contour is not planar.

21. A method of evacuating material from a patient, comprising:
providing the device of claim 1; and
contacting the device with a patient to remove material from the patient.

22. A dental evacuation device for connection to a suction system, the evacuation device comprising:
an elongated member comprising polypropylene, the elongated member extending along a longitudinal axis and having a connection end, a suction end, an inner surface, and an outer surface including a depressed region, the depressed region being depressed toward the longitudinal axis relative to another portion of the outer surface, wherein the inner surface defines a central passageway extending through the member from the connection end to the suction end, the elongated member comprising a transverse aperture disposed between the suction end and the connection end;
a protective tip comprising a cross-linked mixture of ethylene propylene diene monomer rubber and polypropylene, the protective tip being non-releasably secured relative to the elongated member and disposed at least partially within the central passageway and over the depressed region of the elongated member, the protective tip extending from the suction end of the elongated member, the protective tip defining a suction aperture configured to provide access to the central passageway, the protective tip comprising a blunted ridge circumscribing the suction aperture; and
a screening device positioned within the central passageway between the transverse aperture and the connection end, the screening device comprising a plurality of openings configured to allow the passage of liquids and gases through the screening device, wherein the openings are substantially polygonal and have a cross-sectional area of between about 2.0 square millimeters and about 2.5 square millimeters.

23. The evacuation device of claim 22, wherein the screening device is offset from a most distal point of the suction end by a distance that is between 5% and 25% of a maximum longitudinal dimension of the elongated member.

24. A dental evacuation device for connection to a suction system, the evacuation device comprising:
an elongated body member having a connection end, a suction end, an inner surface, and an outer surface including a depressed region, the depressed region being depressed toward the longitudinal axis relative to another portion of the outer surface, wherein the inner surface defines a central passageway extending through the body member from the connection end to the suction end;
a protective means non-releasably secured relative to the elongated body member and disposed over the depressed region and a portion of the inner surface of the elongated body member for protecting a patient from the suction end of the elongated body member; and
a screening means positioned within the central passageway for screening matter passing therethrough.

25. A dental evacuation system comprising:
a delivery device configured to produce a source of negative pressure; and
a dental evacuation device comprising
an elongated body member comprising a first material, the elongated body member extending along a longitudinal axis and having a connection end, a suction end, an inner surface, and an outer surface including a depressed region, the depressed region being depressed toward the longitudinal axis relative to another portion of the outer surface, wherein the inner surface defines a central passageway extending through the body member from the connection end to the suction end,
a protective tip comprising a second material, the protective tip being non-releasably secured relative to the body member and disposed over the depressed region and at least a portion of the inner surface of the body member, the protective tip extending from the suction end of the body member, the protective tip defining a suction aperture configured to provide access to the central passageway, and
a screening device positioned within the central passageway between the connection end and the suction end,
wherein the connection end is configured to connect to the delivery device such that the dental evacuation device is exposed to the source of negative pressure.

26. A dental evacuation device for connection to a suction system, the evacuation device comprising:
an elongated body member comprising a first material, the elongated body member extending along a longitudinal axis and having a connection end, a suction end, an inner surface, an outer surface, and a depressed region, the depressed region being depressed toward the longitudinal axis relative to another portion of the outer surface, wherein the inner surface defines a central passageway extending through the body member from the connection end to the suction end, the elongated body comprising a transverse aperture disposed between the suction end and the connection end and a securement aperture extending transversely through the elongated body member between the suction end and the connection end; and
a protective tip comprising a second material, the protective tip being non-releasably secured relative to the body member and disposed at least partially within the central passageway and the depressed region of the body member, the protective tip extending from the suction end of the body member, the protective tip defining a suction aperture configured to provide access to the central passageway, the protective tip comprising a blunted ridge circumscribing the suction aperture, wherein the blunted ridge comprises a non-planar distal contour,
wherein the first material and the second material are different.

27. The evacuation device of claim 26, wherein the first material comprises polypropylene.

28. The evacuation device of claim 27, wherein the second material comprises a thermoplastic elastomer.

29. The evacuation device of claim 28, wherein the thermoplastic elastomer comprises ethylene propylene monomer rubber.

30. The evacuation device of claim 26, wherein the securement aperture is disposed between the suction end and the transverse aperture.

31. The evacuation device of claim 26, wherein at least a portion of the protective tip is disposed within the securement aperture.

* * * * *